(12) United States Patent
Al-Jabri et al.

(10) Patent No.: US 10,913,694 B2
(45) Date of Patent: Feb. 9, 2021

(54) METHODS FOR FORMING ETHYLBENZENE FROM POLYSTYRENE

(71) Applicants: Saudi Arabian Oil Company, Dhahran (SA); King Abdullah University of Science and Technology, Thuwal (SA)

(72) Inventors: Nouf Mohammed Al-Jabri, Dammam (SA); Kuo-Wei Huang, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 16/513,948

(22) Filed: Jul. 17, 2019

(65) Prior Publication Data

US 2020/0031738 A1 Jan. 30, 2020

Related U.S. Application Data

(60) Provisional application No. 62/711,861, filed on Jul. 30, 2018.

(51) Int. Cl.
*C07C 4/22* (2006.01)
*C07C 15/073* (2006.01)

(52) U.S. Cl.
CPC .............. *C07C 4/22* (2013.01); *C07C 15/073* (2013.01); *C07C 2521/04* (2013.01); *C07C 2523/72* (2013.01); *C07C 2523/745* (2013.01); *C07C 2523/75* (2013.01)

(58) Field of Classification Search
CPC ................. C07C 4/22; C07C 4/02; C07C 4/00
See application file for complete search history.

(56) References Cited

U.S. PATENT DOCUMENTS

| | | |
|---|---|---|
| 3,728,252 A | 4/1973 | Pitchford |
| 4,954,467 A | 9/1990 | Johnson et al. |
| 5,776,423 A | 7/1998 | Feeley et al. |
| 6,930,219 B2 | 8/2005 | Shan et al. |
| 2006/0016723 A1 | 1/2006 | Tang et al. |
| 2006/0088469 A1 | 4/2006 | Perez-Ramirez |
| 2017/0349846 A1 | 12/2017 | Ding et al. |

FOREIGN PATENT DOCUMENTS

| | | |
|---|---|---|
| EP | 3318327 A1 | 5/2018 |
| GB | 416025 A | 9/1934 |

OTHER PUBLICATIONS

Aljabri et al. (Renewable aromatics from the degradation of polystyrene under mild conditions, May 25, 2017, Journal of Saudi Chemical Society, vol. 21, pp. 983-989) (Year: 2017).*
Kijenski et al. (Catalytic degradation of polystyrene, 2005, Polymery, 50, nr 1) (Year: 2005).*

(Continued)

*Primary Examiner* — Youngsul Jeong
(74) *Attorney, Agent, or Firm* — Dinsmore & Shohl LLP

(57) ABSTRACT

According to one or more embodiments presently disclosed, a method of catalytically converting polystyrene may include contacting polystyrene with a catalyst to form a product comprising ethylbenzene. The catalyst may include oxidized iron, oxidized cobalt, and oxidized copper. The catalyst may further include a mesoporous support material with pores having an average pore diameter of from 2 nm to 50 nm.

20 Claims, 11 Drawing Sheets

(56) References Cited

OTHER PUBLICATIONS

International Search Report and Written Opinion dated Oct. 10, 2019 pertaining to International application No. PCT/US2019/042358 filed Jul. 18, 2019, 14 pgs.
International Search Report and Written Opinion dated Oct. 15, 2019 pertaining to International application No. PCT/US2019/042354 filed Jul. 18, 2019, 12 pgs.
International Search Report and Written Opinion dated Oct. 29, 2019 pertaining to International application No. PCT/US2019/042356 filed Jul. 18, 2019, 14 pgs.
Shah, J. et al. "Metal decorated montmorillonite as a catalyst for the degradation of polystyrene" Journal of Taiwan Institute of Chemical Engineers, Aug. 26, 2017, vol. 80, pp. 391-398.
Rehan, M. et al. "Effect of zeolite catalysts on pyrolysis liquid oil" International Biodeterioration & Biodegradation, Dec. 27, 2016, vol. 119, pp. 162-175.
Balakrishnan, R. et al. "Thermal degradation of polystyrene in the presence of hydrogen by catalyst in solution" Polymer Degradation and Stability, Aug. 6, 2007, vol. 92, No. 8, pp. 1583-1591.
Ukei, H. et al. "Catalytic degradation of polystyrene into styrene and a design of recyclable polystyrene with dispersed catalysts" Catalysis Today, Sep. 1, 2000, vol. 62, No. 1, pp. 67-75.
Achilias et al., "Chemical Recycling of Polystyrene by Pyrolysis: Potential Use of the Liquid Product for the Reproduction of Polymer", Macromolecular Materials and Engineering, vol. 292, pp. 923-934, 2007.
Adnan et al., "Polystyrene degradation studies using Cu supported catalysts", Journal of Analytical and Applied Pyrolysis, vol. 109, pp. 196-2004, 2014.
Al-Jabri, "Renewable Aromatics from the Degradation of Polystyrene under Mild Conditions", Thesis, Abstract only, Aug. 2017.
Aljabri et al., "Renewable aromatics from the degradation of polystyrene under mild conditions", Journal of Saudi Chemical Society, vol. 21, pp. 983-989, 2017.
Hart et al., "In situ catalytic upgrading of heavy oil using a pelletized Ni-Mo/Al2O3 catalysts in the THAI process", Journal of Petroleum Science and Engineering, vol. 156, pp. 958-965, 2017.
Ishchenko et al., "The Cu—Co—Fe Oxide System Applied to Carbon Nanotubes Synthesized on Fe2O3", Journal of Superhard Materials, vol. 36, No. 2, pp. 82-88, 2014.
Kaminsky et al., "Feedstock recycling of polymers by pyrolysis in a fluidised bed", Polymer Degradation and Stability, vol. 85, pp. 1045-1050, 2004.
Kijenski et al., "Catalytic degradation of polystyrene", Polimery, 50, nr1, pp. 60-63, 2005.
Kim et al., "Degradation of polystyrene waste over base promoted Fe catalysts", Catalysis Today, vol. 87, pp. 59-68, 2003.
Ramli et al., "Effect of Calcination Method on the Catalytic Degradation of Polystyrene using Al2O3 Supported Sn and Cd Catalysts", Journal of Applied Sciences, 11(8), pp. 1346-1350, 2011.
Shah et al., "Catalytic activity of metal impregnated catalysts for degradation of waste polystyrene", Journal of Industrial and Engineering Chemistry, vol. 20, pp. 3604-3611, 2014.
Shah et al., "Conversion of waste polystyrene through catalytic degradation into valuable products", Korean Journal Chemistry and Engineering, 31(8), pp. 1389-1398, 2014.
Ward et al., "A Two Step Chemo-biotechnological Conversion of Polystyrene to a Biodegradable Thermoplastic", Environmental Science & Technology, 49(7), pp. 2433-2437, 2006.
Zhang et al., "Chemical Recycling of Waste Polystyrene into Styrene over Solid Acids and Bases", Industrial & Engineering Chemistry Research, 34(12), pp. 4514-4519, 1995.
Achilias, D. S., et al. "Chemical Recycling of Polystyrene." Proceedings of the international conference protection and restoration of the environment. vol. 8. 2006.
Al-Jabri, "Renewable Aromatics from the Degradation of Polystyrene under Mild Conditions", Complete Thesis, Published Oct. 2018.
U.S. Office Action dated Aug. 11, 2020 pertaining to U.S. Appl. No. 16/513,970, filed Jul. 17, 2019, 26 pgs.

* cited by examiner

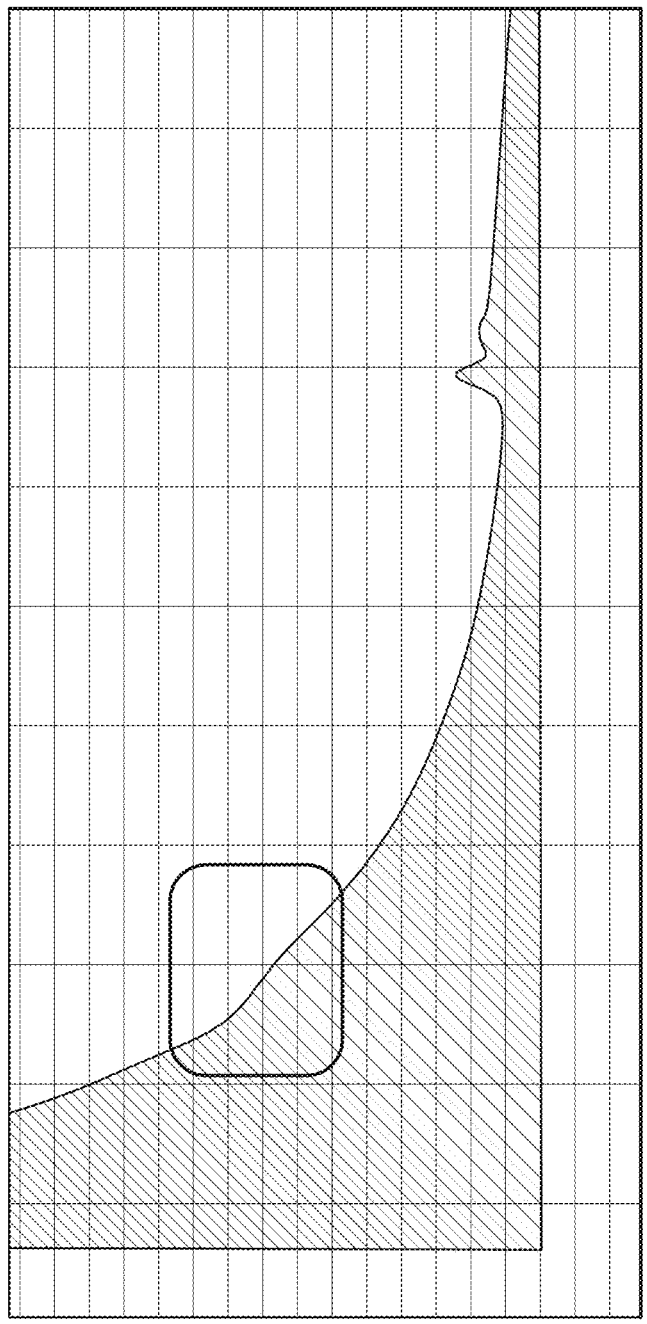

METHODS FOR FORMING ETHYLBENZENE FROM POLYSTYRENE

CROSS REFERENCE TO RELATED APPLICATIONS

The present disclosure claims priority to U.S. Provisional patent application Ser. No. 62/711,861 entitled "METHODS FOR FORMING ETHYLBENZENE FROM POLYSTYRENE," the entirety of which is incorporated by reference in the present disclosure.

BACKGROUND

Field

The present disclosure generally relates to catalysts and, more specifically, to supported, metallic catalysts and methods for the production thereof.

Technical Background

Various chemical processes are facilitated by catalysts. For example, catalysts may be utilized in cracking reactions which break carbon-carbon bonds to form new, smaller molecules. Such cracking reactions may chemically convert substances such as polymers into smaller polymeric or even monomeric units.

BRIEF SUMMARY

Accordingly, there is a need for catalysts which may be useful in various chemical processes such as the conversion of polystyrene. The conversion of polystyrene to ethylbenzene may be useful in polymer recycling. According to one or more embodiments presently described, supported catalysts that include iron, cobalt, and copper may be effective catalysts for processes such as the cracking of polystyrene. The presently described catalysts may convert polystyrene with good selectivity for ethylbenzene formation as compared with other known catalysts. Additionally, such yields of ethylbenzene may be realized at relatively low reaction temperatures (such as, for example 250° C.). Such catalytic activity may allow for efficient recycling of polystyrene into a product including 90 wt. % liquid components at a processing temperature of only 250° C. Other known catalysts may require greater reaction temperatures, such as at least 350° C. and not even achieve as great of liquid yields.

According to one or more embodiments presently described, the catalysts may not only increase reaction rates as compared with conventional catalysts, but may also improve selectivity towards desired products. For example, the presently described catalysts may crack polystyrene with enhanced yields of ethylbenzene as compared to yields of other formed products such as styrene, toluene, or dimers.

In one or more embodiments, the presently described catalysts may be supported on a mesoporous support material and include iron, cobalt, and copper. The iron, cobalt, and copper may be present in the catalyst as oxidized metals (either as compounds that include only one particular metal oxide, or as compounds that include a plurality of metals in an oxidized form). It is believed that the presently disclosed multi-metal catalysts may have favorable catalytic performance as compared with conventional catalysts which contain only one or two metals as catalysts. Such presently described multi-metal catalysts may allow for fine tuning of interaction energies for a particular reaction and may provide multiple catalytic centers for different reaction steps. These properties may offer the presently disclosed multi-metallic catalyst the benefit of cracking with higher efficiencies and product selectivity, even at lower temperatures.

According to one or more additional embodiments, a method of catalytically converting polystyrene may comprise contacting a feed stream comprising polystyrene with a catalyst to form a product stream comprising ethylbenzene. The catalyst may comprise oxidized iron, oxidized cobalt, and oxidized copper. The catalyst may further comprise a mesoporous support material comprising pores having an average pore diameter of from 2 nm to 50 nm.

Although the concepts of the present disclosure are presently described, in one or more embodiments, with primary reference to cracking catalysts for the cracking of petrochemical products such as heavy oils or polystyrenes, it is contemplated that the presently disclosed concepts will enjoy applicability to other catalytic functionality. For example, and not by way of limitation, it is contemplated that the concepts of the present disclosure will enjoy applicability to other catalytic cracking processes which may benefit from the breaking of carbon-carbon bonds.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 8D is a graph depicting scanning transmission electron microscope-electron energy loss spectroscopy of one embodiment of the presently disclosed catalyst, after the catalyst has been used to catalytically crack polystyrene.

DETAILED DESCRIPTION

Figure 1:
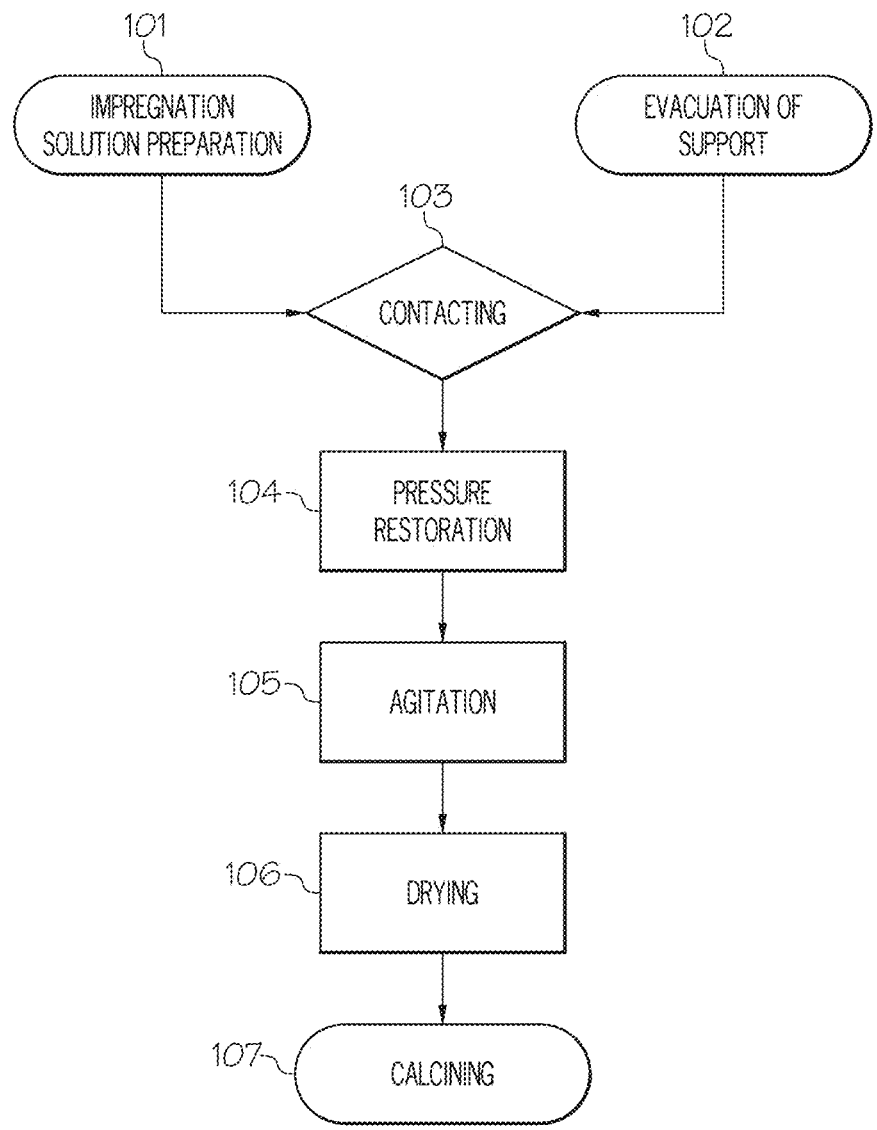
FIG. 1 is a generalized flow chart showing synthesis steps for a supported metallic catalyst, according to one or more embodiments presently disclosed.

The following detailed description describes one or more embodiments of the presently disclosed catalysts. One or more embodiments of the present disclosure are directed to catalysts which may comprise catalytic oxidized metal materials including oxidized iron, oxidized cobalt, and oxidized copper. In some embodiments, the oxidized iron, oxidized cobalt, and oxidized copper may comprise the majority, or all, or the catalytic oxidized metal material in the catalyst. In one or more embodiments, the catalyst may further include a mesoporous support material (sometimes referred to as a "support") comprising pores having an average pore diameter of from 2 nm to 50 nm. Additional embodiments include methods for making such catalysts. The catalysts presently disclosed may be multi-metallic catalysts which include at least three different metals.

Without being limited by theory, it is believed that multi-metallic catalysts having at least three metal compounds differ from monometallic or bimetallic catalysts in structural effects, electronic properties, or both. These properties may, in some cases, present advantages over mono-metallic or bimetallic catalysts in activity, selectivity, or both.

It should be understood that the metals in the multi-metallic catalysts need not be present in their metallic form (that is, as a pure metal). For example, they may be present in their oxide form or in compounds with different metal atoms. For example, iron may be present as $Fe_2O_3$ in the catalysts, or in an oxide compound that includes iron as well as one or more additional metals such as cobalt or copper. Without being limited by theory, it is believed that the choice of metals, their ratios to one another, the choice of catalyst support material, or any combination of these, may play a significant role in the effectiveness of a catalyst.

The presently disclosed catalyst may include catalytic oxidized metal materials comprising at least three oxidized metals (that is, oxidized iron, oxidized cobalt, and oxidized copper). As presently described, an "oxidized metal" may refer to any oxidized elemental metal (such as iron, cobalt, or copper) that is in a chemical compound, such as a metal oxide that includes one or more elemental metals. As such, the oxidized metals of the catalyst may be included in one or more different compounds, where more than one metal oxide is in the same compound. For example, a chemical compound that includes one or more of the oxidized metals, as presently described, may include a single elemental metal in an oxidized state (that is, a single oxidized metal), or may alternatively include multiple elemental metals each in oxidized states (that is, a compound that includes at least two or more elemental metals and oxygen). Elemental metals, as described presently, refer to any metal or metalloid elements of the periodic table. It should be understood that oxidized metals may be present in any oxidation state. The disclosed oxidized metals, such as oxidized iron, oxidized cobalt, and oxidized copper may be in different compounds or all included in a single compound.

According to one or more embodiments, the catalytic oxidized metal materials may comprise at least three metal oxide compounds, where the oxidized iron, the oxidized cobalt, and the oxidized copper are present in separate metal oxide compounds. For example, the catalytic oxidized metal materials may comprise iron oxide, cobalt oxide, and copper oxide. In one or more embodiments, the catalyst may include, without limitation, one or more of iron (II) oxide (FeO), iron (IV) oxide ($FeO_2$), iron (II, III) oxide ($Fe_3O_4$), iron (II, III) oxide ($Fe_5O_6$), iron (II, III) oxide ($Fe_5O_7$, $Fe_{25}O_{32}$, or $Fe_{13}O_{19}$), or iron (III) oxide ($Fe_2O_3$). The catalyst may further include, without limitation, one or more of cobalt (II,III) oxide ($Co_3O_4$), cobalt (II) oxide (CoO), or cobalt (III) oxide ($Co_2O_3$). Without limitation, the catalyst may include one or more of copper (II) oxide (CuO), copper (IV) oxide ($CuO_2$, or $Cu_2O$), or copper (III) oxide ($Cu_2O_3$).

According to some embodiments, at least 95 wt. % of the catalytic oxidized metal materials may be a combination of oxidized iron, oxidized cobalt, and oxidized copper. The weight percent is to be calculated on the basis of all metals in the catalyst, excluding those which are characterized as the support material. Generally, these metallic materials contribute to the catalytic functionality of the catalyst and are disposed on the support material. In one or more embodiments, at least 96 wt. %, at least 97 wt. %, at least 98 wt. %, at least 99 wt. %, at least 99.5 wt. %, or even at least 99.9 wt. %, of the catalytic oxidized metal materials may be a combination of oxidized iron, oxidized cobalt, and oxidized copper. In further embodiments, the catalytic oxidized metal materials may consist essentially of or consist of oxidized iron, oxidized copper, and oxidized cobalt.

According to additional embodiments, the catalytic oxidized metal materials may include any combination of oxidized iron, oxidized cobalt, and oxidized copper in a single compound. For example, the catalytic oxidized metal materials may include a compound formed by any of the iron oxides, cobalt oxides, or copper oxides presently disclosed. Embodiments are contemplated where oxidized iron and oxidized cobalt are present in a single compound, where oxidized iron and oxidized copper are present in a single compound, or where oxidized cobalt and oxidized iron are present in a single compound. Additional embodiments may include a catalyst that comprises a chemical compound that includes oxidized iron, oxidized cobalt, and oxidized copper. For example, and without limitation, iron cobalt oxide ($Fe_2CoO_4$) and copper cobalt oxide ($CuCoO_2$) may be included in the catalyst. In one or more embodiments, the majority of the oxidized iron, oxidized cobalt, an oxidized copper may be present in the form of $Fe_2O_3$, $Cu_2O$, CuO, and $Co_3O_4$.

In one or more embodiments, the weight ratio of iron atoms:cobalt atoms:copper atoms in the catalyst may be from 1:0.4-0.6:0.5-0.7. For example, in one or more embodiments, the weight ratio of iron atoms:cobalt atoms in the catalyst may be from 1:0.4 to 1:0.42, from 1:0.42 to 1:0.44, from 1:0.44 to 1:0.46, from 1:0.46 to 1:0.48, from 1:0.48 to 1:0.5, from 1:0.5 to 1:0.52, from 1:0.52 to 1:0.54, from 1:0.54 to 1:0.56, from 1:0.56 to 1:0.58, from 1:0.58 to 1:0.6, or any combination thereof. For example, in one or more embodiments, the weight ratio of iron atoms:copper atoms in the catalyst may be from 1:0.50 to 1:0.52, 1:0.52 to 1:0.54, from 1:0.54 to 1:0.56, from 1:0.56 to 1:0.58, from 1:0.58 to 1:0.6, from 1:0.6 to 1:0.62, from 1:0.62 to 1:0.64, from 1:0.64 to 1:0.68, from 1:0.68 to 1:0.70, or any combination thereof. It should be understood that ranges are contemplated that include multiple sub-ranges presently disclosed. It should be understood that when a ratio of three components is disclosed, that any two of those components are contemplated to have a defined ratio as presently described.

Without being bound by theory, it is believed that when at least some reactions take place on a supported catalyst, properties of the catalyst support material may affect the reaction. For example, properties of the catalyst support material that may affect catalytic functionality include one or more of the solubility of the support in relevant solvents, the surface area of the support, the pore size of the support, and the acidity of the support.

According to one or more embodiments, the catalyst support may be mesoporous. Without being bound by any particular theory, another characteristic of a catalytic support that may affect catalytic performance may be the pore size. Porous materials can be defined as microporous materials, mesoporous materials, and macroporous materials. Microporous materials have pore diameters less than 2 nm, mesoporous materials have pore diameters from 2 nm to 50 nm, and macroporous materials have pore diameters of greater than 50 nm. In this application the categories microporous, mesoporous, and macroporous are all used to refer to the average pore diameter because the diameter of each individual pore will vary. Because some materials may have clusters of average sizes or be hierarchical with vastly different pore structures, it is possible for one material to have multiple pore diameter characterizations. For example, an activated carbon may be mesoporous, microporous, or both, depending on the synthesis method.

While pore size may have an effect on surface area, in a catalyst, pore size also may help to affect which reagents can reach the catalytic centers located within the pores. Therefore, without being limited by theory, it is believed that catalyst pore size may affect both activity and selectivity. The presently described catalysts may include mesoporous support materials such as one or more of silica, alumina, alumosilicates, or activated carbon.

According to one or more embodiments, the surface area of the catalyst may be greater than or equal to 100 square meters per gram ($m^2/g$). For example, surface area of the catalyst may be greater than or equal to 125 $m^2/g$, greater than or equal to 150 $m^2/g$, greater than or equal to 175 $m^2/g$, greater than or equal to 200 $m^2/g$, greater than or equal to 225 $m^2/g$, or even greater than or equal to 250 $m^2/g$. The surface area of the catalyst may majorly be a function of the support material. The surface area of a catalyst support material may be significant for determining the utilization ratio of the catalyst bonded to the support surface. Without being limited by theory, it is believed that only catalytic centers which are accessible by reagents can participate in the reaction and, therefore, catalytic centers inaccessible by reagents are essentially wasted. By providing a relatively great surface area support, it is believed that smaller catalyst particles with a relatively greater surface area/volume ratio may be used. Surface area of a support is traditionally described in units of surface area to mass, such as $m^2/g$ or surface area to volume, such as square meters per cubic meters ($m^2/m^3$). Determining the actual surface area of a catalyst support material is often performed by a molecular adsorption test such as the Brunauer-Emmett-Teller (BET) surface area measurement.

According to one or more embodiments, the surface area of the mesoporous support material may be less than or equal to 700 square meters per gram ($m^2/g$). It has been unexpectedly found that lower surface area mesoporous support material may lead to increased production of liquid products in, for example, reactions involving the cracking of polystyrene or petroleum tar. Without being limited by theory, it is believed that larger surface area mesoporous support materials preferentially favor oligomerization pathways. This preference for oligomerization pathways may prevent the production of valuable liquid products. For example, surface area of the mesoporous support material may be less than or equal to 600 $m^2/g$, less than or equal to 500 $m^2/g$, less than or equal to 450 $m^2/g$, less than or equal to 400 $m^2/g$, less than or equal to 350 $m^2/g$, less than or equal to 300 $m^2/g$, less than or equal to 250 $m^2/g$, less than or equal to 200 $m^2/g$, less than or equal to 150 $m^2/g$, less than or equal to 100 $m^2/g$, or even less than or equal to 50 $m^2/g$.

According to one or more embodiments, the catalyst, the support, or both, may be insoluble in any liquids present during the reaction. Immiscibility of the catalyst support in the relevant solvent may ensure the heterogeneity of a catalytic reaction. Heterogeneous catalytic reactions may be desired over homogenous catalytic reactions due to the ease of separation of products and catalyst. A heterogeneous catalytic reaction is defined in this disclosure as one in which the catalyst and at least some of the products are in different phases. For example, the reaction of a solid phase catalyst with a solid phase reactant and at least one liquid or gas phase product, is referred to as heterogeneous.

According to one or more embodiments, the mesoporous support material may comprise alumina material, such as gamma alumina. As used in this disclosure, "alumina material," also sometimes referred to as "aluminum oxide" or "alumina" in the present disclosure, is a category of materials sharing the chemical formula $Al_2O_3$. Alumina material, in one or more embodiments, may be a suitable catalyst support due to one or more of its amphoteric nature, relatively great surface area, relatively lesser cost, relatively great thermal conductivity, insolubility in aqueous solvents, or mesoporous structure. Alumina material can be formed into a variety of structures including, but without limitation, alumina, alpha alumina, beta alumina, gamma alumina, and theta alumina. Alpha alumina is believed to have a relatively lesser surface area and little to no catalytic activity. Beta alumina is believed to be hexagonal with somewhat greater surface area. In one or more embodiments, gamma alumina may be the most desirable phase for use in catalysts due to one or more of its relatively great specific surface area, relatively great activity, good temperature resistance, and mesoporosity. According to one or more embodiments, the catalyst may be thermally stable to a temperature greater than 500° C., such as greater than 750 degrees Celsius (° C.), greater than 1000° C., or even greater than 1500° C.

In one or more embodiments, the support material may comprise at least 95 weight percent (wt. %), at least 96 wt. %, at least 97 wt. %, at least 98 wt. %, at least 99 wt. %, at least 99.5 wt. %, at least 99.9 wt. % of alumina, or even consist of alumina. Without being limited by theory, it is believed that for some reactions, such as those described presently, alumina has a good surface acidity level, which can produce liquid products from polystyrene or petroleum tars. It is further believed that aluminum/silica hybrids (referred to as aluminosilicates and aluminum silicate) have elevated surface acidity levels relative to pure alumina. Therefore, when the support material comprises relatively great amounts of aluminum/silica hybrid (for example, greater than 5 wt. %, 10 wt. %, or 25 wt. %), it tends to favor crosslinking reactions and prevent the production of liquid products.

In additional embodiments, the support material may comprise at least 50 wt. %, at least 75 wt. %, at least 95 wt. %, or even at least 99 wt. % of gamma alumina.

According to one or more embodiments, the mesoporous support material may comprise silica material. As used in this disclosure, silica material, also referred to sometimes in this disclosure as "silica" or "silicon dioxide," is a category of materials sharing the chemical formula $SiO_2$. In some catalytic reactions, silica material may present an advantage over alumina material due to the absence of acidic sites. Pure silica materials may be present as alpha-quartz, beta-quartz, alpha-tridymite, beta tridymite, alpha-cristobalite, beta-cristobalite, 2 dimensional silica sheets, and many other structures. In one or more embodiments, the support material may comprise at least 50 wt. %, at least 75 wt. %, at least 95 wt. %, or even at least 99 wt. % of silica material.

In one or more additional embodiments, the catalyst may comprise a hierarchical structured material comprising a silicate or aluminosilicate. For example, the catalysts may be supported on Mobil Composition of Matter number 41 (MCM-41). Mixed alumina-silica materials, referred to as aluminosilicates, present some of the advantages of both alumina and silica materials. These mixed materials may also be formed in to a material with a hierarchical structure, such as MCM-41. As used in this disclosure, MCM-41 refers to a family of mesoporous silica or aluminosilicates materials with a specific hierarchical structure. Without being limited by theory it is believed that, unlike zeolites, MCM-41 has no Bronstead acid centers and its acidity is comparable to that of amorphous aluminosilicates. This acidity comparable to amorphous aluminosilicates makes MCM-41 a suitable support for reactions where crosslinking of polymers is undesirable.

In one or more embodiments, the support material may comprise at least 50 wt. %, at least 75 wt. %, at least 95 wt. %, or even at least 99 wt. % of one or more hierarchical structured materials, such a hierarchical structures aluminosilicates. In additional embodiments, the support material may comprise at least 50 wt. %, at least 75 wt. %, at least 95 wt. %, or even at least 99 wt. % of MCM-41.

In one or more additional embodiments, the catalyst support may comprise activated carbon. Generally, activated carbon is a form of carbon processed to have increased porosity which causes an increased surface area. Activated carbon may have pores of one or more diameters based on the processing conditions by which it may be produced. It may also have been further activated through chemical modifications to its surface. Activated carbon may present an inexpensive, relatively great surface area catalyst support with tunable pore sizes. In one or more embodiments, the support material may comprise at least 50 wt. %, at least 75 wt. %, at least 95 wt. %, or even at least 99 wt. % of activated carbon.

In one or more embodiments, the catalyst support material may be substantially free of zeolites. One common class of catalyst support materials is the zeolite. Zeolites tend to have a relatively great acidity and a microporous structure. This greater acidity can negatively affect some reactions. For example, it is believed that the greater acidity of a zeolite may cause crosslinking reactions when a polystyrene is present. These crosslinking reactions may inhibit the degradation of the polystyrene. Without being limited by theory, it is believed that micropores, such as the pores on a zeolite, may be of insufficient size such that they may be blocked by certain reagents such as a polystyrene side group.

According to one or more embodiments, the catalyst may be substantially free of carbon nanotubes. Generally, carbon nanotubes are a form of carbon processed into a cylindrical nanostructure. They may take forms including single wall (SWNT) and multi wall (MWNT), with diameters ranging from 0.3 nm to 100 nm. The carbon nanotube structures are not truly porous but are more similar to a graphene sheet formed into a tube. Without being limited by theory, it is believed that due to their structure, carbon nanotubes can have extreme surface area to mass ratios. It is believed that carbon nanotubes may present challenges in catalytic situations due to their tendency towards agglomeration and the possibility that reaction products may block entry into the tube section of carbon nanotubes.

According to one or more embodiments, the combined weight of iron atoms, cobalt atoms, and copper atoms in the catalyst may be from 0.1 percent (%) to 20% of total weight of the catalyst. The ratio of active catalytic metal material to catalyst support materials may have a substantial effect on both catalytic activity and cost. Generally, catalyst support materials are less expensive than active catalytic metal materials. Due to this cost differential, it may be desirable to minimize the loading of active catalytic metal materials to the extent this may be possible without affecting activity or selectivity. For example, in one or more embodiments, a combined weight of the iron atoms, cobalt atoms, and copper atoms in the catalyst may be from 0.001% to 0.01%, from 0.01% to 0.1%, from 0.1% to 0.5%, from 0.5% to 1%, from 1% to 2%, from 2% to 3%, from 3% to 4%, from 4% to 5%, from 5% to 6%, from 6% to 7%, from 7% to 8%, from 8% to 9%, from 9% to 10%, from 10% to 11%, from 11% to 12%, from 12% to 13%, from 13% to 14%, from 14% to 15%, from 15% to 16%, from 16% to 17%, from 17% to 18%, from 18% to 19%, from 19% to 20%, or any combination thereof. It should be understood that ranges are contemplated that include multiple sub-ranges presently disclosed.

According to some embodiments, at least 95 wt. % of the catalyst may be a combination of the catalytic oxidized metal materials and the mesoporous support material. That is, each of the discrete catalyst particles comprises at least 95 wt. %, at least 96 wt. %, at least 97 wt. %, at least 98 wt. %, at least 99 wt. %, or at least 99.5 wt. % of the combination of catalytic oxidized metal materials and the mesoporous support material.

Generally, methods of production may have a significant effect on the final characteristics of a catalyst. In some cases, methods of production of the presently disclosed catalyst may affect the location of catalytic sites, oxidation states of catalytic metals, crystal structure, and bonds between catalytic materials.

According to one or more embodiments, a method of making a catalyst may comprise contacting an iron precursor, a copper precursor, and a cobalt precursor with a mesoporous support material to form an impregnated support material, and calcining the impregnated support material to form the catalyst. The catalyst may comprise oxidized iron, oxidized cobalt, and oxidized copper, which may be formed from the precursors. In one or more embodiments, such as depicted in FIG. 1, such a method may include additional steps for the preparation of the catalyst, as is subsequently described.

FIG. 1 depicts a flow chart of one or more embodiments of forming the presently described catalyst. According to one or more embodiments as described in FIG. 1, the method of making the catalyst may comprise an impregnation solution preparation step 101, a catalyst support material evacuation step 102, a contacting step 103 where the impregnation solution may contact the evacuated catalyst support material, a pressure restoration step 104, an agitation step 105, a drying step 106, and a calcining step 107.

Still referring to FIG. 1, the method may comprise an impregnation solution preparation step 101. The impregnation solution preparation step may comprise contacting catalytic precursors with a solvent to form an impregnation solution. The impregnation solution preparation step may further comprise agitating or mixing of the impregnation solution prior to the contacting of the impregnation solution with the mesoporous support material. The solvent may be water, or an acid, or a base, or an organic liquid, or an ionic liquid, or any other substance capable of dissolving the metal precursors. As is presently described, the catalytic precursors may include the material of the metal in the catalyst, such as iron, cobalt, copper, or any combination of these.

In one or more embodiments, the presently disclosed catalysts may be prepared from metal precursors. Generally, the metal precursors (that is, an iron precursor, a copper precursor, and a cobalt precursor) are converted to form the metals in the catalyst. For example, metallic portions of the precursor may become the metallic components of the catalyst and other organic constituents of the precursors may be burned off in the catalyst formation process.

In one or more embodiments, the metal precursors may be soluble in the chosen solvent of the precursor solution. One important characteristic of a metal precursor in liquid synthesis procedures, such as the ones described in this disclosure, may be the compatibility of the metal precursor with the chosen solvent. Without being limited by theory, it is believed that a metal precursor which does not dissolve in a chosen solvent may not achieve sufficient dispersion to effectively coat a catalyst support material.

In one or more embodiments, catalytic precursors may include iron nitrate nonahydrate ($Fe(NO_3)_3 \cdot 9H_2O$), copper nitrate trihydrate ($Cu(NO_3)_2 \cdot 3H_2O$), and cobalt nitrate hexahydrate ($Co(NO_3)_2 \cdot 6H_2O$). In additional embodiments, iron precursors may include iron (II) succinate ($C_4H_6FeO_4$), ferric acetylacetonate ($C_{15}H_{21}FeO_6$), iron (III) chloride ($FeCl_3$), iron (II) chloride ($FeCl_2$), iron (II) acetate ($Fe(C_2H_3O_2)_2$), or any other suitable iron-containing compound where the elements other than iron can be removed by heating or oxidation. In alternate embodiments, copper precursors may include copper (I) acetate ($C_2H_3CuO_2$), copper (II) sulfate ($CuSO_4$), copper (II) acetate ($C_4H_6CuO_4$), bis(acetylacetonate)copper(II) ($C_{10}H_{14}CuO_4$), or any other suitable copper-containing compound where the elements other than copper can be removed by heating or oxidation. In alternate embodiments, cobalt precursors may include cobalt (II) chloride —$CoCl_2$, cobalt (II) acetate (($CH_3O_2)_2$), cobalt acetylacetonate ($Co(C_5H_7O_2)_3$), or any other cobalt containing compound where the elements other than cobalt can be removed by heating or oxidation.

Still referring to FIG. 1, the catalyst support material evacuation step 102 may comprise evacuating the mesoporous support material prior to the mesoporous support material being contacted with the iron precursor, the copper precursor, and the cobalt precursor. Still referring to FIG. 1, and without being limited by theory, it is believed that when a mesoporous support material is evacuated (step 102), and then contacted with an impregnation solution (step 103), then undergoes a pressure restoration step 104, the resulting pressure difference between the pores and the ambient air may help to overcome surface tension and push the impregnation solution into the pores. As used in this disclosure, the term evacuation means to hold under a vacuum for a period of time. It should be understood that as used in this disclosure, the term "vacuum" does not only refer to an absolute vacuum, as it also may refer to any pressure less than atmospheric pressure, such as an absolute pressure of less than 755 Torr, 700 Torr, 600 Torr, 400 Torr, 100 Torr, 10 Torr, 1 Torr, or 0.001 Torr.

According to some embodiments, the evacuation step 102 may comprise holding the mesoporous support material under vacuum, for a duration of time, at a temperature of, for example, from 80° C. to 90° C., from 90° C. to 100° C., from 100° C. to 110° C., from 110° C. to 120° C., from 120° C. to 130° C., or even greater than 130° C., or any combination of these ranges. According to some embodiments, the duration of time may be from 1 minute (min) to 10 minutes (min), from 10 min to 20 min, from 20 min to 40 min, from 40 min to 80 min, from 80 min to 160 min, from 160 min to 300 min, from 300 min to 600 min, from 600 min to 1200 min, from 1200 min to 2400 min, from 2400 min to 4800 min, or greater than 4800 min, or any combination of these ranges.

Still referring to FIG. 1, the agitation step 105 may comprise agitating the impregnated support material at a temperature of from 40° C. to 80° C., such as from 40° C. to 50° C., from 50° C. to 60° C., from 60° C. to 70° C., from 70° C. to 80° C., or any combination thereof. It should be understood that the term agitate is intended to mean any action which causes increased interactions between molecules within a solution, such as, but without limitation, stirring, sonication, shaking, mixing, and the like. According to one or more embodiments, agitation of the support material occurs for 3 hours at a temperature of 60° C., from 40° C. to 50° C., from 50° C. to 60° C., from 60° C. to 70° C., from 70° C. to 80° C., or any combination thereof.

According to described embodiments, the impregnation of the mesoporous support material may comprise contacting the mesoporous support material with a solution comprising one or more metal catalyst precursors. For example, the support material may be submerged in the solution comprising the one or more metal catalyst precursors, an impregnation method sometimes referred to as a saturated impregnation. In embodiments of saturated impregnation, the support may be submerged in an amount of solution comprising the metal catalyst precursors 2 to 4 times of that which is absorbed by the support, and the remaining solution is subsequently removed. According to another embodiment, the impregnation may be by incipient wetness impregnation, sometimes referred to as capillary impregnation or dry impregnation. In embodiments of incipient wetness impregnation, the metal catalyst precursor containing solution is contacted with the support, where the amount of solution is approximately equal to the pore volume of the support and capillary action may draw the solution into the pores.

Referring again to FIG. 1, the method may comprise a drying step 106 that may include drying the impregnated support material. The drying may be under vacuum at a temperature of from 80° C. to 150° C. According to one or more embodiments, drying the impregnated support material may occur under a vacuum at a temperature of from 80° C. to 90° C., from 90° C. to 100° C., from 100° C. to 110° C., from 110° C. to 120° C., from 120° C. to 150° C., or any combination thereof. It should be understood that ranges are contemplated that include multiple sub-ranges presently disclosed.

Still referring to FIG. 1, the method may further comprise a calcining step 107 that may comprise heating the impregnated support material at a temperature greater than 450° C. Generally, the International Union of Pure and Applied Chemistry (IUPAC) defines calcining or calcination as a process of heating to relatively great temperatures in air or oxygen. However, calcination may also refer to thermal treatment in the absence or partial absence of oxygen with the intent to bring about thermal decomposition. According to some embodiments, after the contacting of the support material with the solution, the support material may be calcined at a temperature of at least 450° C., or at least 500° C., (such as from 500° C. to 600° C.) for a time of at least 3 hours (such as 3 hours to 6 hours). For example, the calcining may be at a temperature of 550° C. for 4 hours. Generally, the impregnation process will allow for attachment of the metal catalyst onto the support materials (that is, the zeolite and metal oxide support). The metal catalyst precursors may include one or more of iron (Fe), copper (Cu), cobalt (Co), and following the impregnation, are present on the catalyst support as compounds comprising Fe, Cu, Co, or combinations thereof. While these metal catalyst materials may include metal oxides, it should be appreciated that the metal catalyst materials are distinct from the mesoporous support material of the catalyst which may, in some embodiments, be alumina.

In one or more embodiments, the presently disclosed catalysts may have good catalytic functionality for converting polystyrene into ethylbenzene. Generally, polystyrene is one of the most widely produced and used polymers, made up of repeating styrene monomers. Polystyrene has a relatively great energy density but is usually not recycled. It is believed that industry may desire a method to convert polystyrene to more active constituent chemicals, such as ethylbenzene. According to one or more embodiments, a method of catalytically converting polystyrene may comprise contacting polystyrene with a catalyst to form a product which may comprise ethylbenzene, where the catalyst may comprise oxidized iron. According to one or more additional embodiments, a method of catalytically converting polystyrene may comprise contacting a feed stream comprising polystyrene with a catalyst to form a product stream comprising ethylbenzene.

According to one or more embodiments, the feed stream that is converted by contact with the catalyst may comprise at least 50 wt. % polystyrene, such as at least 50 wt. % polystyrene, at least 60 wt. % polystyrene, at least 70 wt. % polystyrene, at least 80 wt. % polystyrene, at least 90 wt. % polystyrene, at least 95 wt. % polystyrene, or even at least 99 wt. % polystyrene. The feed stream may comprise a liquid, a solid, a colloid, or any other chemical state. For example the feed stream may comprise polystyrene particles, polystyrene floating on water, polystyrene mixed with acetone, melted polystyrene, or any combination thereof.

According to one or more embodiments, the polystyrene may be in a liquid phase when contacted with the catalyst. It should be understood that the polystyrene need not be in a solid phase when first contacted with the catalyst and that it may be converted to a liquid phase while in contact with the catalyst. For example, solid polystyrene may be introduced to the catalyst at 25° C. and the temperature may be raised to 250° C., where the now liquid polystyrene may contact with the catalyst.

According to one or more embodiments, the polystyrene may be contacted with the catalyst in an atmosphere comprising one or more of oxygen, an inert gas, or a reducing gas. For example the polystyrene may be contacted with the catalyst in an atmosphere comprising air or the polystyrene may be contacted with the catalyst in an atmosphere enriched in one or more constituents relative to air. Without being limited by any particular theory, it is believed that increasing concentrations of hydrogen may increase reaction rates. According to one or more embodiments, the polystyrene may be contacted with the catalyst in an atmosphere which comprises greater than 1 mole percent (mol. %) hydrogen, greater than 5 mol. % hydrogen, greater than 10 mol. % hydrogen, greater than 25 mol. % hydrogen, greater than 50 mol. % hydrogen, greater than 75 mol. % hydrogen, greater than 90 mol. % hydrogen, or even greater than 99 mol. % hydrogen. Without being limited by any particular theory, it is believed that sufficient hydrogen may be released from cracking of the polystyrene and that selectivity may be improved by not having additional hydrogen. According to some embodiments, the atmosphere may comprise less than 1 mol. % oxygen or from 1 mol. % to 5 mol. % oxygen, from 5 mol. % to 15 mol. % oxygen, from 15 mol. % to 20 mol. % oxygen, from 20 mol. % oxygen to 22 mol. % oxygen, from 22 mol. % oxygen to 30 mol. % oxygen, from 30 mol. % oxygen to 40 mol. % oxygen, from 40 mol. % oxygen to 50 mol. % oxygen, from 50 mol. % oxygen to 75 mol. % oxygen, from 75 mol. % oxygen to 90 mol. % oxygen, from 90 mol. % oxygen to 95 mol. % oxygen, from 95 mol. % oxygen to 99 mol. % oxygen, or any combination thereof.

According to some embodiments, the polystyrene may be contacted with the catalyst at a temperature of less than 350° C. while still maintaining relatively good catalytic conversion performance. For example, the polystyrene may be contacted with the catalyst at a temperature of less than 350° C., or less than 325° C., less than 300° C., less than 275° C., or less than 250° C. According to some embodiments, the polystyrene may be contacted with the catalyst at a temperature of from 100° C. to 125° C., from 125° C. and 150° C., from 150° C. and 175° C., from 175° C. and 200° C., from 200° C. and 225° C., from 225° C. and 240° C., from 240° C. and 260° C., from 260° C. and 275° C., from 275° C. and 300° C., from 300° C. and 325° C., from 325° C. and 350° C., or any combination thereof. It should be understood that the polystyrene may contact the catalyst at a temperature less than this range and the temperature may be increased until it falls within this range. For example, in some embodiments, the polystyrene may contact the catalyst at a temperature of 25° C. and the temperature may be increased to 250° C. at a predetermined rate.

According to some embodiments, the polystyrene may contact the catalyst within one of a fluidized bed reactor, a continuous stirred tank reactor, a batch reactor, a stirred tank reactor, a slurry reactor, or a moving bed reactor. According to some embodiments, the polystyrene may contact the catalyst within any reactor suitable for heterogeneous chemical reactions. It should be understood that the polystyrene need not first contact the catalyst within the reactor. For example, in some embodiments, the polystyrene may contact the catalyst in a feed pipe and then both the polystyrene and the catalyst may be in contact within the reactor.

According to some embodiments, the product comprising ethylbenzene may comprise a liquid phase and a solid phase. According to some embodiments, the weight ratio of the liquid phase to the solid phase may be at least 2:1 at 25° C. For example the weight ratio of the liquid phase to the solid phase at 25° C. may be at least 2:1, at least 3:1, at least 4:1, at least 5:1, at least 6:1, at least 7:1, at least 8:1, at least 9:1, at least 10:1, at least 11:1, or any combination thereof. The solid phase may comprise unreacted polystyrene, crosslinked styrene material, solid catalyst material, and char. The liquid phase may comprise ethylbenzene, solvent, toluene, styrene, cumene, alpha-methylstyrene, and dimers. It should be understood that the products may be formed at a greater temperature than 25° C., such as 250° C., where more of the product may be a gas. For example the product ethylbenzene has a boiling point of 136° C. and may therefore be a gas at the reaction conditions but a liquid at 25° C.

According to some embodiments, the product stream may comprise a liquids fraction at 25° C. The liquid fraction may comprise at least 25 wt. % of the carbon material in the original polystyrene. For example, the liquid fraction may comprise at least 25 wt. %, at least 50 wt. %, at least 75 wt. %, at least 80 wt. %, at least 85 wt. %, at least 90 wt. %, at least 95 wt. %, or even at least 90 wt. % of the carbon material in the original polystyrene. The liquids fraction may comprise ethylbenzene, solvent, toluene, styrene, cumene, alpha-methylstyrene, and dimers.

According to some embodiments, the liquid phase of the product stream may be greater than 60 mol. % ethylbenzene. For example, the liquid phase may be greater than 60 mol. % ethylbenzene, greater than 70 mol. % ethylbenzene, greater than 80 mol. % ethylbenzene, or even, greater than 90 mol. % ethylbenzene. It should be understood that the presently disclosed ratios may be taken at 25° C. because ethylbenzene may be a gas at temperatures greater than 136° C.

In one or more embodiments, the presently disclosed catalysts may be utilized to crack petroleum hydrocarbons such as, without limitation, tars. According to one or more embodiments, a method of catalytically cracking a petroleum hydrocarbon may comprise contacting the petroleum hydrocarbon feed with the presently disclosed catalyst to form upgraded petroleum hydrocarbons. As presently described, the contacting of the petroleum hydrocarbon by the catalyst forms an "upgraded petroleum hydrocarbon" which may have one or more of reduced density (greater API gravity), reduced viscosity, or reduced average molecular weight. Generally, the upgraded petroleum hydrocarbons are greater in value than the pre-processed petroleum hydrocarbons that have not been contacted with the catalyst.

As presently described, "petroleum hydrocarbons" may refer to chemical compositions that comprise oil such as crude petroleum materials and/or products refined from petroleum oils, such as gasoline and diesel. For example, petroleum hydrocarbons may include liquid crude oils, tar sands, residuals from crude oil refining, and middle distillates from crude oil refining. It is contemplated that the petroleum hydrocarbons which may be cracked by the presently disclosed catalyst may be in a feed stream that includes at least 50 weight percent wt. %, at least 75 wt. %, at least 95 wt. %, or even at least 99 wt. % of the respective, disclosed types of petroleum hydrocarbons.

According to some embodiments, the petroleum hydrocarbon feed may have an American Petroleum Institute (API) gravity of less than or equal to 40 degrees (°). According to some embodiments, the petroleum hydrocarbon may have an API gravity of less than or equal to 35 degrees, 30 degrees, 22.3 degrees, 20 degrees, 10 degrees, 8 degrees, 6 degrees, or even 4 degrees. Generally, API gravity is a measure of how heavy or light a petroleum liquid is compared to water.

According to one or more embodiments, the petroleum hydrocarbons that are processed may include tar such as tar sands, also known as bituminous sands or oil sands. Generally, tar sands are defined as reservoirs containing oil too viscous to flow in sufficient quantities for economic production. While tar sands may have a relatively lesser economic value, their economic value may be increased though catalytic upgrading as presently described.

In one or more embodiments, the petroleum hydrocarbon feed may comprise crude oil. As used in this disclosure, crude oil may be a mixture of different hydrocarbons. The crude oil may be unprocessed or it may be pre-processed for removal of undesirable materials such as sulfur, heavy metals, nitrogen, and other like contaminants. Generally crude oil may contain light distillates, middle distillates, and residue. The middle distillates and residue may be catalytically cracked or converted into more valuable components. According to some embodiments, the petroleum hydrocarbon feed may comprise middle distillates or residue or both. Middle distillates may include hydrocarbons having a boiling point between 200° C. and 300° C. Residues may include hydrocarbons having a boiling point greater than 300° C.

According to some embodiments, the petroleum hydrocarbons of the feed may have a viscosity greater than 100 centipoises at reservoir temperature. For example the petroleum hydrocarbon may have a viscosity greater than 100 centipoises, greater than 500 centipoises, greater than 1,000 centipoises, greater than 2,000 centipoises, greater than 5,000 centipoises, greater than 10,000 centipoises, or even greater than 15,000 centipoises, at reservoir temperature, or any combination thereof. It should be understood that viscosity may be a function of temperature and as such viscosity measurements may be taken at a defined temperature. Reservoir temperature is understood to mean the undisturbed temperature in the reservoir. For example if a reservoir were 50° C. before drilling and superheated steam were used to raise the average reservoir temperature to 90° C., the viscosity at 50° C. should be used for this measurement.

According to one or more embodiments, the petroleum hydrocarbons may be contacted with the catalyst at a temperature of from 100° C. to 1000° C. For example the petroleum hydrocarbons may be contacted with the catalyst at a temperature of from 100° C. to 200° C., from 200° C. to 300° C., from 300° C. to 400° C., from 400° C. to 500° C., from 500° C. to 600° C., from 600° C. to 700° C., from 700° C. to 800° C., from 800° C. to 900° C., from 900° C. to 1000° C., or any combination thereof. It should be understood that ranges are contemplated which include multiple sub-ranges presently disclosed.

According to one or more embodiments, the upgraded petroleum hydrocarbon (which may be all or a portion of a product stream) may have an API gravity of at least 1 degree greater than the petroleum hydrocarbon feed. For example, the product stream may have an API gravity of 1 degree, 2 degrees, 3 degrees, 4 degrees, 5 degrees, 10 degrees, 15 degrees, 20 degrees, 25 degrees, 30 degrees, 35 degrees, 40 degrees, greater than the petroleum hydrocarbon feed in its pre-cracked state.

In one or more embodiments, the presently disclosed catalysts may be utilized for cracking of petrochemical crude feedstocks in a subterranean environment. According to one or more embodiments, a method for reducing the viscosity of a subterranean petroleum hydrocarbon may comprise heating a subterranean petroleum hydrocarbon within a petroleum hydrocarbon reservoir and contacting the heated subterranean petroleum hydrocarbon with a catalyst to reduce the viscosity of the subterranean petroleum hydrocarbon. It should be understood that both the heating step and the contacting steps may be carried out underground. As used in this disclosure, a petroleum hydrocarbon reservoir refers to an underground deposit of petroleum hydrocarbons, such as tar.

According to one or more embodiments, the method may further comprise igniting a subterranean combustion zone within the petroleum hydrocarbon reservoir. As used in this disclosure, a subterranean combustion zone refers to any underground area of sustained combustion of petroleum hydrocarbons. For example, according to some embodiments, the subterranean combustion zone may comprise fire flooding. Generally, fire flooding is a method of thermal recovery in which a flame front is generated in the reservoir by igniting a fire at the sandface of an injection well. Generally, the sandface of an injection well may refer to the interface between the reservoir and the well. Injection of oxygen containing gasses may then be used to help maintain the flame front. Without being limited by any particular theory, it is believed that the resultant, steam, heat, and pressure from the flame front may drive heavy oil to the production wells. It is believed that the heat may cause some degree of thermally induced cracking but further upgrading may still be desired by industry.

According to some embodiments, the catalyst and a production well are structurally configured such that the heated petroleum hydrocarbons may contact a catalyst within a production well. As used in this disclosure, a production well is a device which may be used to remove petroleum hydrocarbons from a petroleum hydrocarbon reservoir. Generally, the catalyst may form a packing within the production well. The catalyst may be granular, porous, or formed into shapes such a Rasching rings, Berl saddles, Intalox saddles, or any other shape capable of promoting solid to liquid contact. Without being limited by theory, it is believed that the useful lifetime of a catalyst bed may be extended when the reaction occurs in a plug flow configuration. In such a configuration, the rate of catalyst inactivation may differ along the length of the pipe, constantly exposing new sections of catalyst to unreacted heavy oil.

According to some embodiments the catalyst and a production well are structurally configured such that the heated petroleum hydrocarbons may contact the catalyst as the heated petroleum hydrocarbons enter the production well. For example, the catalyst bed may constitute an annulus around the production well. The annulus may be within the production well or the annulus may be around the exterior of the production well. Heated petroleum hydrocarbons may enter the production well at perforated intervals and the heated petroleum hydrocarbons may contact the catalyst at these perforated intervals, either inside or outside of the production well.

According to some embodiments, the catalyst may be dispersed within a gravel pack surrounding a production well. Generally a gravel pack may include gravel of a specific size placed around a production well. Without being limited by theory, it has been shown that the dispersal of a catalyst around a production well may yield similar results to packing within the production well while eliminating some technical barriers. Improved dispersion may yield relatively greater catalyst utilization rates and increased space for catalyst may help to offset catalyst deactivation.

The presently described processes may be useful for the catalytic cracking of petroleum hydrocarbons, both underground in an oil formation or in a refinery. For example, when the cracking is performed underground, it may be particularly useful for reducing the viscosity of tars so that they may be more easily and cost-efficiently transported to the surface. In other embodiments, the presently described catalysts may be used in refining operations and coupled with one or more refining processes for forming desired products from crude oils. These processes may have advantages such as relatively lesser operating temperature, relatively increased operating lifetimes, and relatively greater conversion rates compared with conventional cracking catalysts.

EXAMPLES

Using the embodiments of the present disclosure, catalyst systems were produced which exemplify the catalytic attributes presently described. It should be understood that the ensuing Examples are illustrative of one or more embodiments presently disclosed, and should not be construed in any way as limiting on the appended claims or other portions of the present application. It should be understood that in the following examples, references to Fe, Cu, and Co may refer to oxidized iron, oxidized copper, and oxidized cobalt respectively; for example, FeCuCo/alumina may refer to oxidized iron, oxidized copper, and oxidized cobalt, all supported on alumina where the FeCuCo comprises three separate oxide compounds, or oxide compounds with two or more of Fe, Cu, or Co.

Example 1—Preparation of Fe—Cu—Co/alumina

To prepare a sample of the 1 weight percent (wt. %) multi-metallic catalyst, 5.0 grams (g) of gamma-alumina was evacuated overnight. $Fe(NO_3)_3 \cdot 9H_2O$, $Cu(NO_3)_2 \cdot 3H_2O$, and $Co(NO_3)_2 \cdot 6H_2O$ were measured and mixed with deionized water to form an impregnation solution. The evacuated gamma-alumina was sonicated for 10 minutes, then the impregnation solution was added to the alumina in a quantity slightly greater than the alumina pore volume. The resulting mixture was then stirred at 60° C. for 3 hours, then dried in a vacuum oven overnight at 110° C. Finally, the dried $FeCuCo/Al_2O_3$ was calcined at 550° C. for 4 hours (hr) in air.

Table 1 gives a comparison of the raw alumina support used in Example 1 and the prepared FeCuCo/Alumina catalyst of Example 1. It can be seen that the BET surface area and the pore volume both decreased after impregnation of the support although the pore size did not change. This is believed to indicate that the pore structure remained constant while some of the pores became filled with oxidized metals.

TABLE 1

| Catalyst | BET Surface Area ($m^2/g$) | Pore Size (nm) | Pore Volume (centimeters cubed per gram ($cm^3/g$)) |
| --- | --- | --- | --- |
| Raw Alumina Support | 256.31 | 13.16 | 0.84 |
| FeCuCo/Alumina | 208.90 | 12.13 | 0.64 |

Figure 2A:
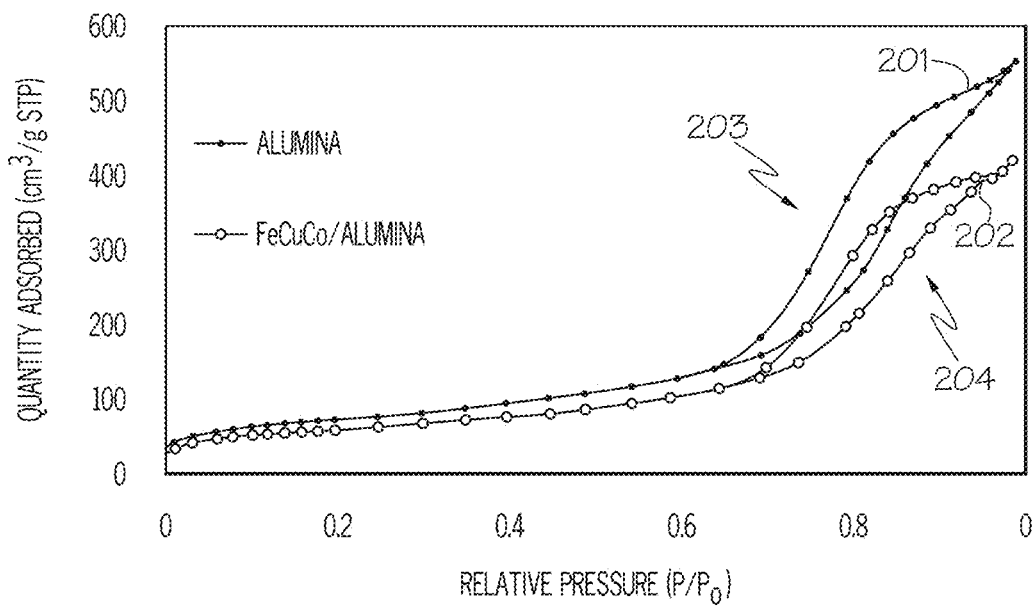
FIG. 2A is a graph showing the adsorption/desorption behavior of nitrogen on one embodiment of the presently disclosed catalyst and its support material.

FIG. 2A gives the nitrogen adsorption-desorption isotherm of the alumina catalyst support 201 and the FeCuCo/alumina catalyst 202 of Example 1. The pattern of type IV hysteresis shown in hysteresis loops 203 (alumina) and 204 (FeCuCo/alumina) indicate that the nitrogen is being adsorbed onto a mesoporous solid via multilayer adsorption followed by capillary condensation.

Figure 2B:
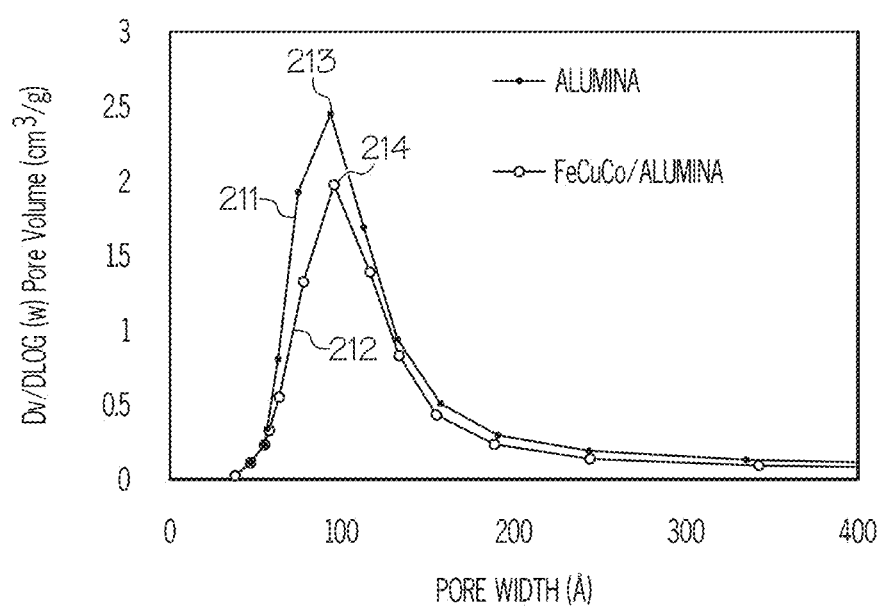
FIG. 2B is a graph showing the pore size distribution of one embodiment of the presently disclosed catalyst and its support material.

FIG. 2B gives the pore size distribution of the alumina catalyst support 211 and the FeCuCo/alumina catalyst 212.

Figure 3A:
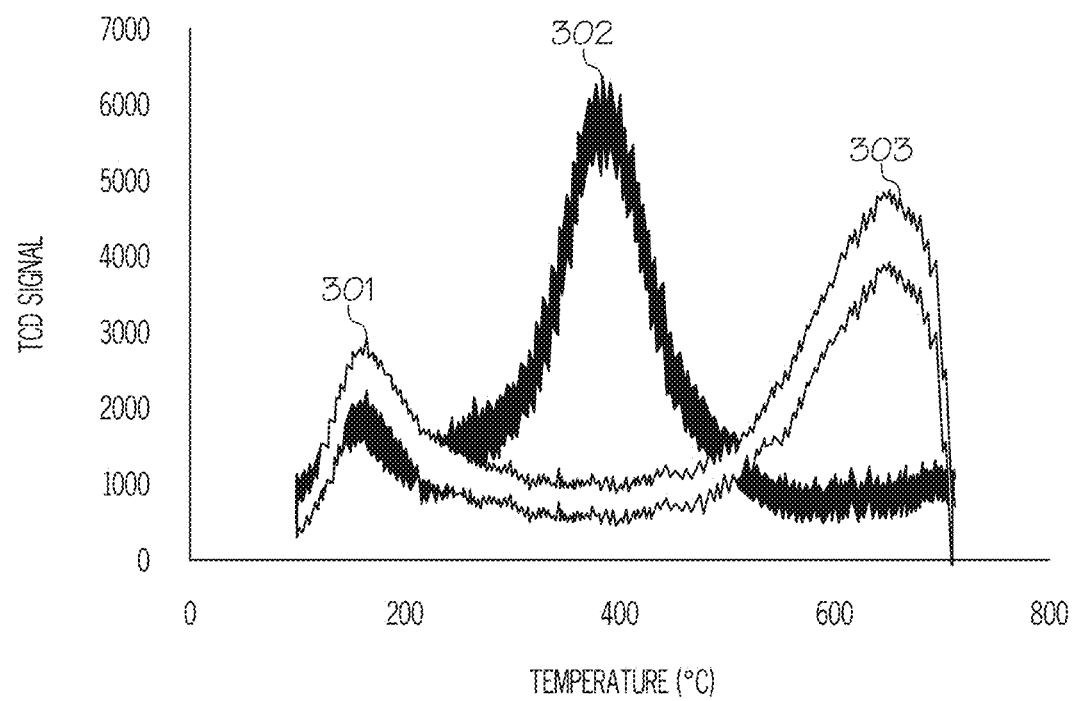
FIG. 3A is a graph showing the carbon dioxide ($CO_2$) temperature programmed desorption (TPD) behavior of one embodiment of the presently disclosed catalyst and its support material.
Figure 3B:
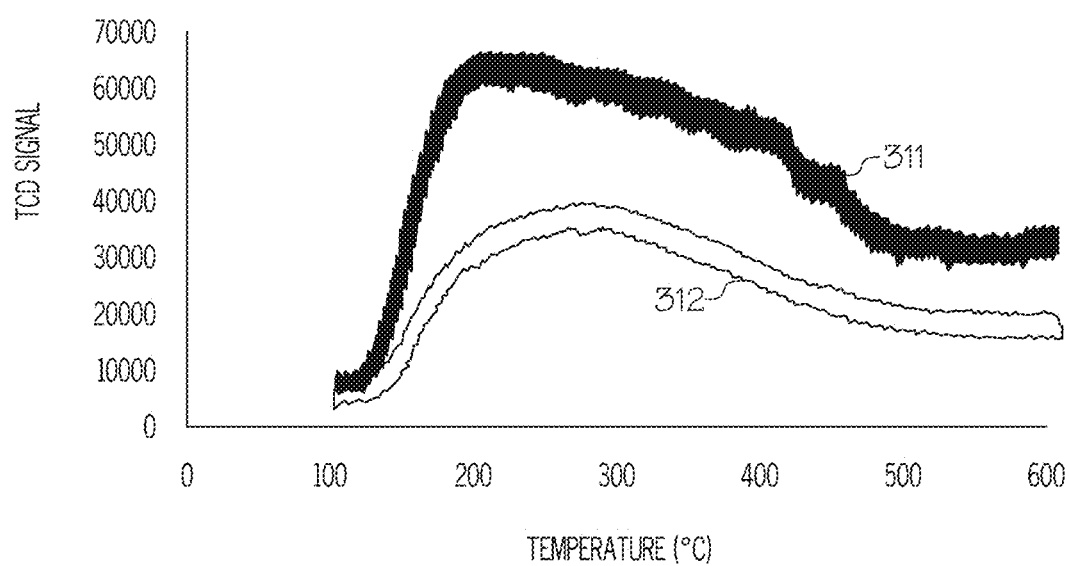
FIG. 3B is a graph showing the ammonia ($NH_3$) temperature programmed desorption behavior of one embodiment of the presently disclosed catalyst and its support material.

Both samples have peak pore size concentrations centered around 100 angstroms, shown at 213 (alumina) and 214 (FeCuCo/alumina). Generally, $CO_2$ temperature programmed desorption (TPD) can be used to determine basicity of a solid. FIG. 3A shows the $CO_2$ TPD for the raw alumina used in Example 1 and the FeCuCo/alumina catalyst formed in Example 1. Both the alumina and the FeCuCo/alumina curves show a peak at 301 roughly consistent in size. The synthesis procedure in Example 1 appears to remove the peak at 303 and creates a new medium strength basicity peak 302 around 400° C. Generally, $NH_3$ temperature programmed desorption (TPD) can be used to determine the acidity of a solid. FIG. 3B shows the $NH_3$ TPD curves for the raw alumina 312 used in Example 1 and the FeCuCo/alumina catalyst 311 formed in Example 1. The change in intensity after the addition of FeCuCo to the alumina support indicates an increase in acidity. It is believed that the increase in acidity is due to the Lewis acidity of iron.

Figure 4A:
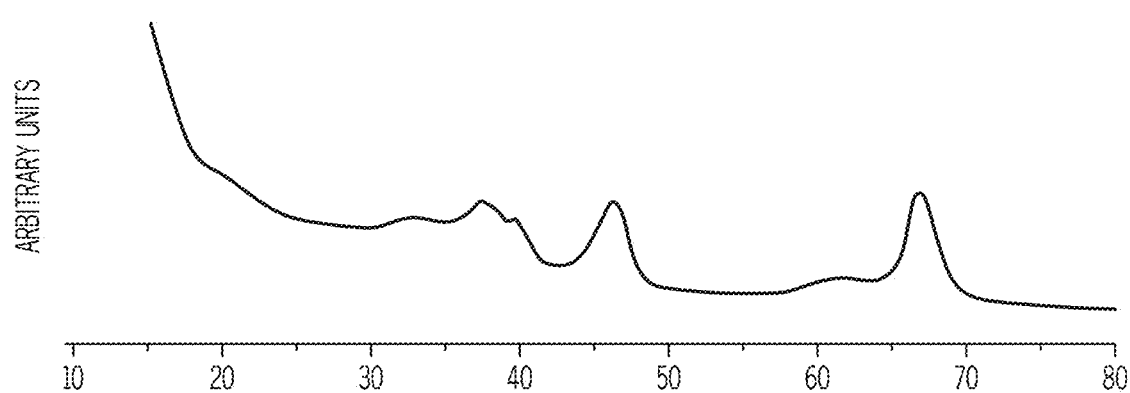
FIG. 4A provides the x-ray diffraction (XRD) pattern of one embodiment of the presently disclosed mesoporous support material.
Figure 4B:
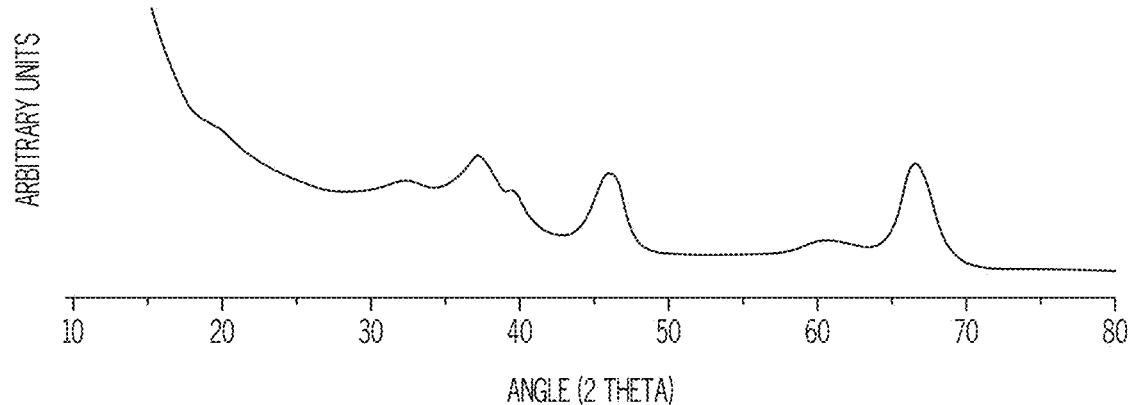
FIG. 4B provides the x-ray diffraction pattern of one embodiment of the presently disclosed catalyst.

FIG. 4A shows the X-ray diffraction (XRD) pattern of the parent aluminum oxide and FIG. 4B shows the XRD pattern of the FeCuCo/alumina catalyst. There is no significant difference between the XRD pattern of the FIGS. 4A and 4B. This is believed to suggest good dispersion of the Fe—Cu—Co on the alumina support. The diffraction peaks appear at 19.8°, 32°, 37.1°, 39.4°, 45.9°, 61.1° and 66.8° which corresponds to (111), (220), (331), (222), (400), (511) and (440) which matches the gamma-Al2O3 XRD pattern.

Example 2—Conversion of Polystyrene to Ethylbenzene

To convert polystyrene to ethylbenzene, 2.0 g of polystyrene were combined with from 200 mg and 500 mg of the catalyst from Example 1, in a 25 mL reaction vessel. The resulting mixture was stirred and heated under air at a ramp rate of 4° C./min to a final temperature of 250° C. and held at 250° C. for 90 minutes. The Comparative Example data of Table 2 is supplied from Kijenski, J. and T. Kaczorek, Catalytic degradation of polystyrene. Polimery, 2005, 50(1): p. 60-63.

TABLE 2

| | Catalyst | Liquid Yield % | Rxn Temp (° C.) | Atmosphere |
|---|---|---|---|---|
| Comparative Example A | Nickel molybdenum alumina (NiMo/$Al_2O_3$) | 70 | 375 | Hydrogen ($H_2$) |
| Comparative Example B | NiMo/$Al_2O_3$ | 70.9 | 400 | Nitrogen ($N_2$) |
| Comparative Example C | Cobalt molybdenum alumina (CoMo/$Al_2O_3$) | 77.3 | 375 | $H_2$ |
| Comparative Example D | CoMo/$Al_2O_3$ | 72.6 | 400 | $N_2$ |
| Comparative Example E | Iron cobalt silica (FeCo/$SiO_2$) | 80.5 | 375 | $H_2$ |
| Comparative Example F | FeCo/$SiO_2$ | 71.9 | 400 | $N_2$ |
| Example 2 | FeCuCo/$Al_2O_3$ | 90 | 250 | Air |

Referring now to Table 2, it can be seen that only the present disclosure provides the desired combination of relatively greater liquid yield and relatively lesser reaction temperature for the catalytic degradation of polystyrene.

Figure 5A:
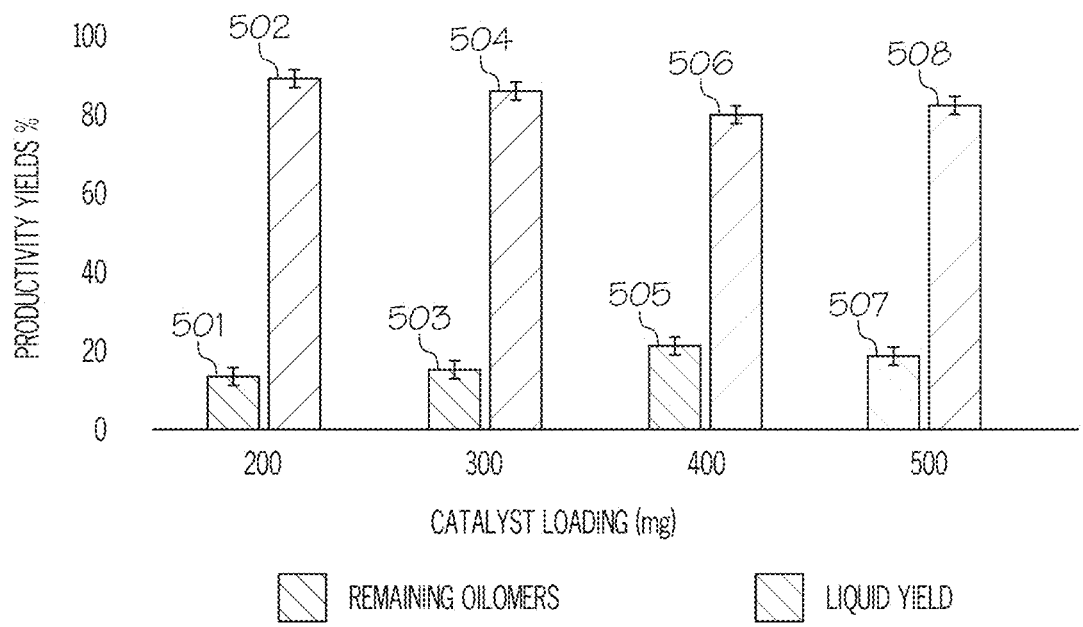
FIG. 5A is a graph showing the influence of catalyst loading on the ratio of liquid to solid yields for the catalytic cracking of polystyrene by the presently disclosed catalyst.

FIG. 5A shows the relationship between catalyst loading and liquid yields for the reaction of Example 2. 501, 503, 505, and 507 show the liquid yield percentages for a catalyst loading of 200 milligrams (mg), 300 mg, 400 mg, and 500 mg, respectively. 502, 504, 506, and 508, show the liquid yield percentages for a catalyst loading of 200 mg, 300 mg, 400 mg, and 500 mg, respectively.

Figure 5B:
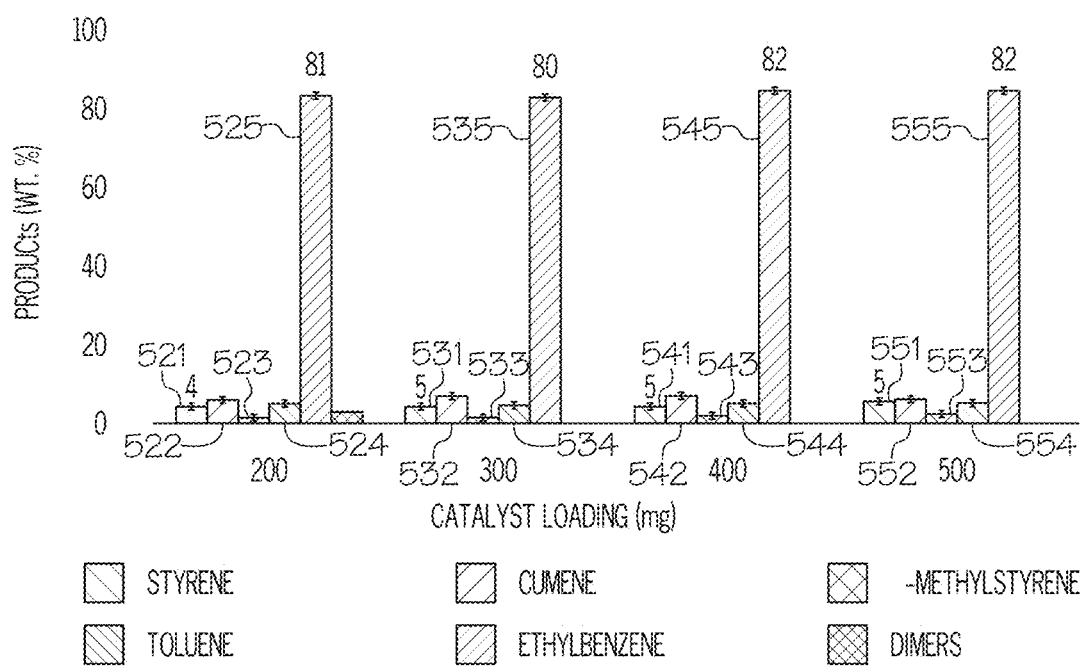
FIG. 5B is a graph showing the influence of catalyst loading on the ratio of different liquid products for the catalytic cracking of polystyrene by the presently disclosed catalyst.

FIG. 5B shows the relationship between catalyst loading and the constituents of the liquid products. In all cases the yield of ethylbenzene is equal to or greater than 80%. 521, 531, 541, and 551 show the yield of styrene for a catalyst loading of 200 mg, 300 mg, 400 mg, and 500 mg, respectively. 522, 532, 552, and 552 show the yield of cumene for a catalyst loading of 200 mg, 300 mg, 400 mg, and 500 mg, respectively. 523, 533, 543, and 553 show the yield of alpha-methystyrene for a catalyst loading of 200 mg, 300 mg, 400 mg, and 500 mg, respectively. 524, 534, 544, and 554 show the yield of toluene for a catalyst loading of 200 mg, 300 mg, 400 mg, and 500 mg, respectively. 525, 535, 545, and 555 show the yield of ethylbenzene for a catalyst loading of 200 mg, 300 mg, 400 mg, and 500 mg, respectively.

Figure 6B:
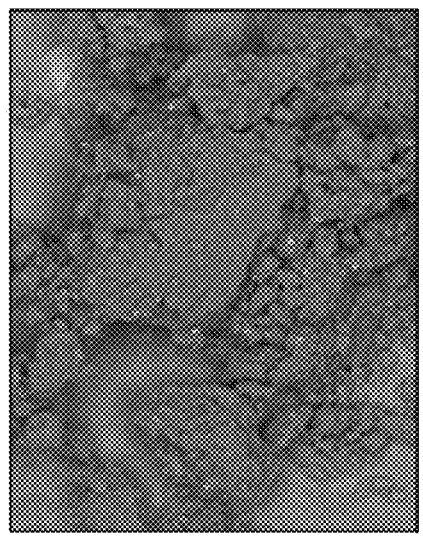
FIG. 6B is a scanning electron microscope image of one embodiment of the presently disclosed catalyst, after the catalyst has been used to catalytically crack polystyrene.
Figure 6A:
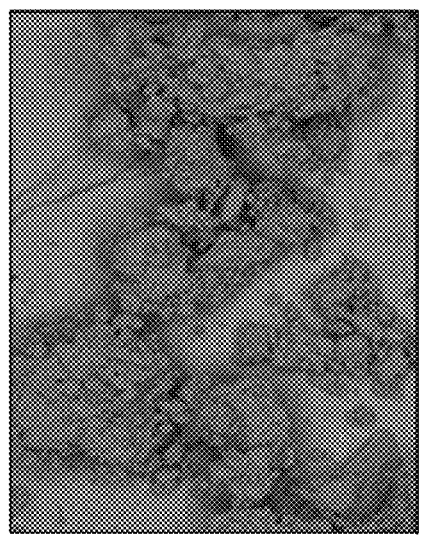
FIG. 6A is a scanning electron microscope (SEM) image of one embodiment of the presently disclosed catalyst.

FIG. 6A shows a scanning electron microscope (SEM) image of the FeCuCo/alumina catalyst of Example 1. This figure shows the lack of metal clusters indicating homogenous distribution of the oxidized iron, oxidized cobalt, and oxidized copper within the support. FIG. 6B shows a SEM image of the FeCuCo/alumina catalyst of Example 1 after the process of Example 2. The white dots 601 in this figure are believed to be metal clusters which have aggregated during the reaction.

Figure 7B:
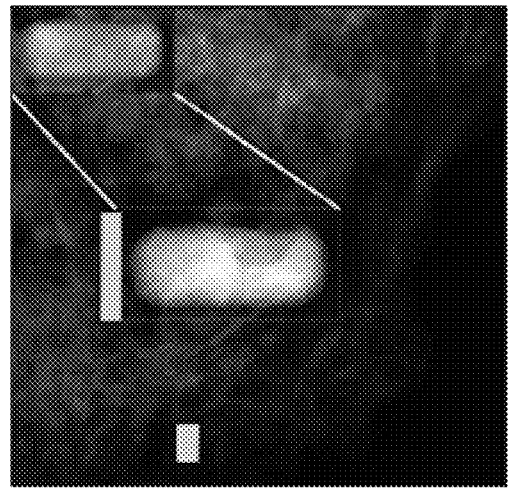
FIG. 7B is a scanning transmission electron microscope image of one embodiment of the presently disclosed catalyst, after the catalyst has been used to catalytically crack polystyrene.
Figure 7A:
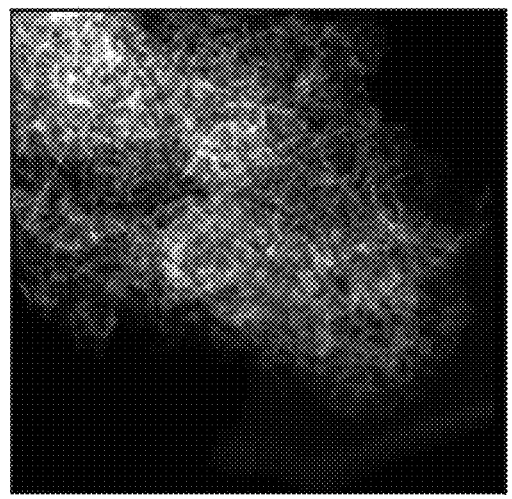
FIG. 7A is a scanning transmission electron microscope (STEM) image of one embodiment of the presently disclosed catalyst.

FIG. 7A shows a scanning transmission electron microscope (STEM) image of the catalyst of Example 1. The catalyst appears to have a nest like structure which was not disturbed by the reaction as shown in FIG. 7B. FIG. 7B shows a STEM image of the spent catalyst of Example 2.

Figure 8A:
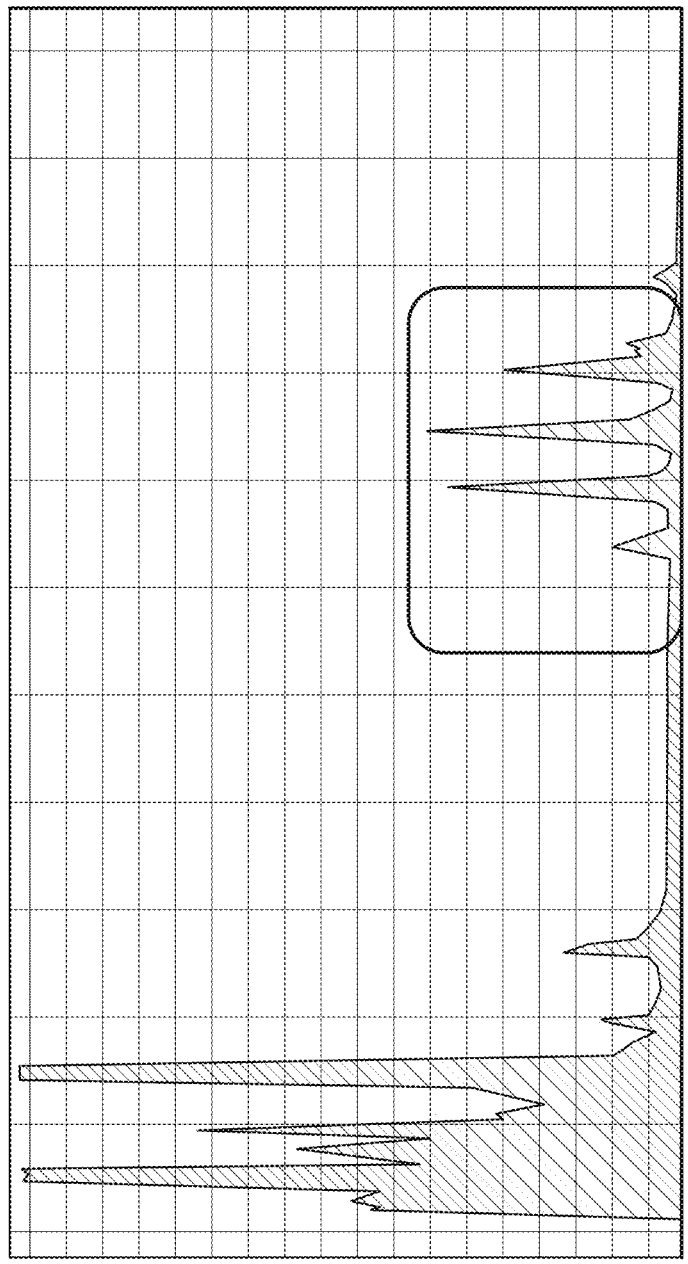
FIG. 8A is a graph depicting scanning transmission electron microscope-energy dispersive spectroscopy of one embodiment the presently disclosed catalyst.
Figure 8B:
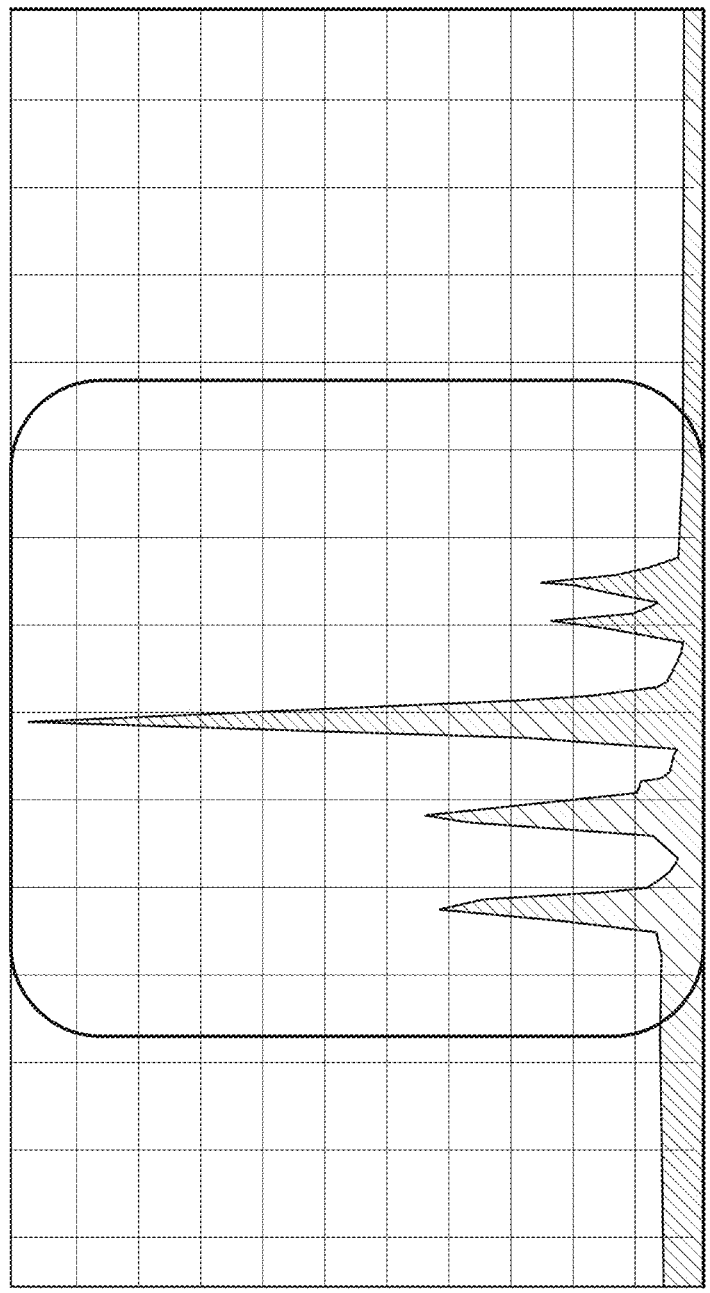
FIG. 8B is a graph depicting scanning transmission electron microscope-energy dispersive spectroscopy (STEM-EDS) of one embodiment of the presently disclosed catalyst, after the catalyst has been used to catalytically crack polystyrene.
Figure 8C:
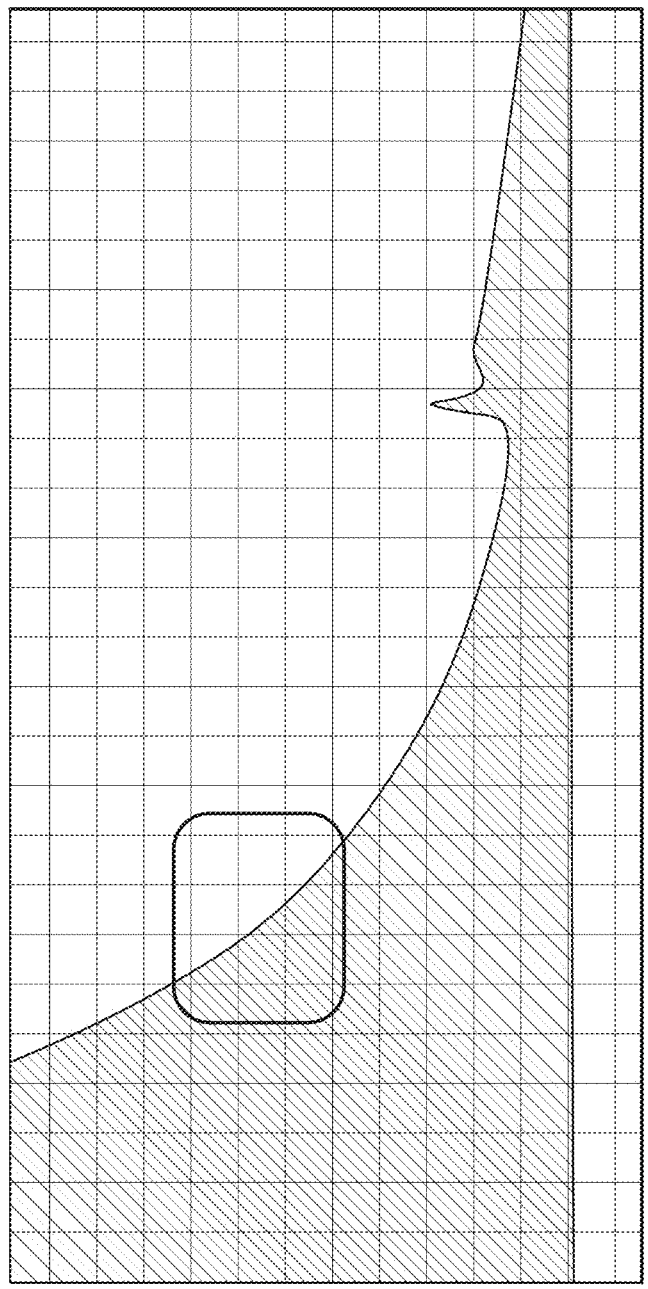
FIG. 8C is a graph depicting scanning transmission electron microscope-electron energy loss spectroscopy (STEM-EELS) of one embodiment of the presently disclosed catalyst.

FIG. 8A shows scanning transmission electron microscope-energy dispersive spectroscopy (STEM-EDS) of the FeCuCo/alumina of Example 1. FIG. 8B shows STEM-EDS signals of spent FeCuCo/alumina from Example 2. FIG. 8C shows scanning transmission electron microscope-electron energy loss spectroscopy (STEM-EELS) of the FeCuCo/Alumina of Example 1. FIG. 8D shows STEM-EELS of spent FeCuCo/alumina from Example 2.

For the purposes of describing and defining the present subject matter, it is noted that reference to a characteristic of the subject matter of the present disclosure being a "function of" a parameter, variable, or other characteristic is not intended to denote that the characteristic is exclusively a function of the listed parameter, variable, or characteristic. Rather, reference to a characteristic that is a "function" of a listed parameter, variable, etc., is intended to be open ended such that the characteristic may be a function of a single parameter, variable, etc., or a plurality of parameters, variables, etc.

It is also noted that recitations in this disclosure of "at least one" component, element, etc., should not be used to create an inference that the alternative use of the articles "a" or "an" should be limited to a single component, element, etc.

It is noted that recitations of a component of the present disclosure being "configured" in a particular way, to embody a particular property, or to function in a particular manner, are structural recitations, as opposed to recitations of intended use. More specifically, the references to the manner in which a component is "configured" denotes an existing physical condition of the component and, as such, is to be taken as a definite recitation of the structural characteristics of the component.

Having described the subject matter of the present disclosure in detail and by reference to specific embodiments thereof, it is noted that the various details presently disclosed should not be taken to imply that these details relate to elements that are essential components of the various embodiments presently described, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are presently identified as preferred or particularly advantageous, it is contemplated that the present disclosure is not necessarily limited to these aspects.

It is noted that one or more of the following claims utilize the term "where" as a transitional phrase. For the purposes of defining the present subject matter, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A method of catalytically converting polystyrene, the method comprising:
    contacting polystyrene with a catalyst to form a product comprising ethylbenzene, where the catalyst comprises:
        catalytic oxidized metal materials comprising:
            oxidized iron;
            oxidized cobalt; and
            oxidized copper; and
        a mesoporous support material comprising pores having an average pore diameter of from 2 nm to 50 nm,
    wherein a weight ratio of iron atoms:cobalt atoms:copper atoms in the catalyst is 1:0.4-0.6:0.5-0.7.

2. The method of claim 1, where the polystyrene is in a liquid phase when contacted with the catalyst.

3. The method of claim 1, where the polystyrene is contacted with the catalyst in an atmosphere comprising one or more of oxygen, an inert gas, or a reducing gas.

4. The method of claim 1, where:
    the product comprising ethylbenzene comprises a liquid phase and a solid phase; and
    a weight ratio of liquid phase to solid phase is at least 2:1 at 25° C.

5. The method of claim 4, where the liquid phase comprises greater than 60 mole percent ethylbenzene.

6. The method of claim 1, where the polystyrene contacts the catalyst within one of a fluidized bed reactor, a continuous stirred tank reactor, a batch reactor, a stirred tank reactor, a slurry reactor, or a moving bed reactor.

7. The method of claim 1, where the mesoporous support material comprises alumina material or silica material.

8. The method of claim 1, where the mesoporous support material comprises gamma alumina.

9. The method of claim 1, where at least 95 wt. % of the catalytic oxidized metal materials are a combination of the oxidized iron, the oxidized cobalt, and the oxidized copper.

10. The method of claim 1, where at least 95 wt. % of the mesoporous support material comprises alumina.

11. The method of claim 1, where at least 95 wt. % of the catalyst is a combination of the catalytic oxidized metal materials and the mesoporous support material.

12. A method of catalytically converting polystyrene, the method comprising:
    contacting a feed stream comprising polystyrene with a catalyst to form a product stream comprising ethylbenzene, where the catalyst comprises:
        catalytic oxidized metal materials comprising:
            oxidized iron;
            oxidized cobalt; and
            oxidized copper; and
        a mesoporous support material comprising pores having an average pore diameter of from 2 nm to 50 nm,
    wherein a weight ratio of iron atoms:cobalt atoms:copper atoms in the catalyst is 1:0.4-0.6:0.5-0.7.

13. The method of claim 12, where the feed stream comprises at least 50 wt. % of polystyrene.

14. The method of claim 12, where the product stream comprises a liquids fraction at 25° C.

15. The method of claim 12, where the liquids fraction comprises at least 60 mole percent ethylbenzene.

16. The method of claim 12, where:
    the mesoporous support material comprises alumina material.

17. The method of claim 12, where at least 95 wt. % of the catalytic oxidized metal materials are a combination of the oxidized iron, the oxidized cobalt, and the oxidized copper.

18. The method of claim 12, where at least 95 wt. % of the mesoporous support material comprises alumina.

19. The method of claim 1, where the polystyrene is contacted with the catalyst at a temperature of less than 350° C.

20. The method of claim 12, where the feed stream is contacted with the catalyst at a temperature of less than 350° C.

* * * * *